United States Patent [19]

Brock

[11] Patent Number: 5,000,683
[45] Date of Patent: Mar. 19, 1991

[54] PERIODONTAL PROBE

[76] Inventor: David L. Brock, 3 Warwick Dr., Long Valley, N.J. 07853

[21] Appl. No.: 521,400

[22] Filed: May 10, 1990

[51] Int. Cl.⁵ .......................... A61C 19/04; A61C 3/00
[52] U.S. Cl. ...................................... 433/72; 433/141; 433/75
[58] Field of Search ...................... 433/72, 141, 32, 75

[56] References Cited

U.S. PATENT DOCUMENTS

| | | | |
|---|---|---|---|
| 4,203,223 | 5/1980 | Lautenschlager et al. | 433/75 |
| 4,445,857 | 5/1984 | Borst | 433/75 |
| 4,708,647 | 11/1987 | Pippin et al. | 433/32 |
| 4,764,114 | 8/1988 | Jeffcoat et al. | 433/72 |

Primary Examiner—John J. Wilson
Assistant Examiner—C. Cherichetti
Attorney, Agent, or Firm—Kenneth P. Glynn

[57] ABSTRACT

The present invention is directed toward a handheld dental instrument which automatically regulates the pressure at which the working end of the instrument engages a person's teeth or gums. The instrument includes a probe that is spring biased into a set position. The bias of the probe is predetermined, and is designed to yield to a preset minimum force. The deformation of the instrument's spring bias keeps the force of the instrument consistent against any object. This consistent pressure assures that the instrument will work in the same manner, and give the same results, time after time. Additionally, the consistency of the instrument will result in more accurate results and increase in the dentist's confidence while using the instrument.

8 Claims, 3 Drawing Sheets

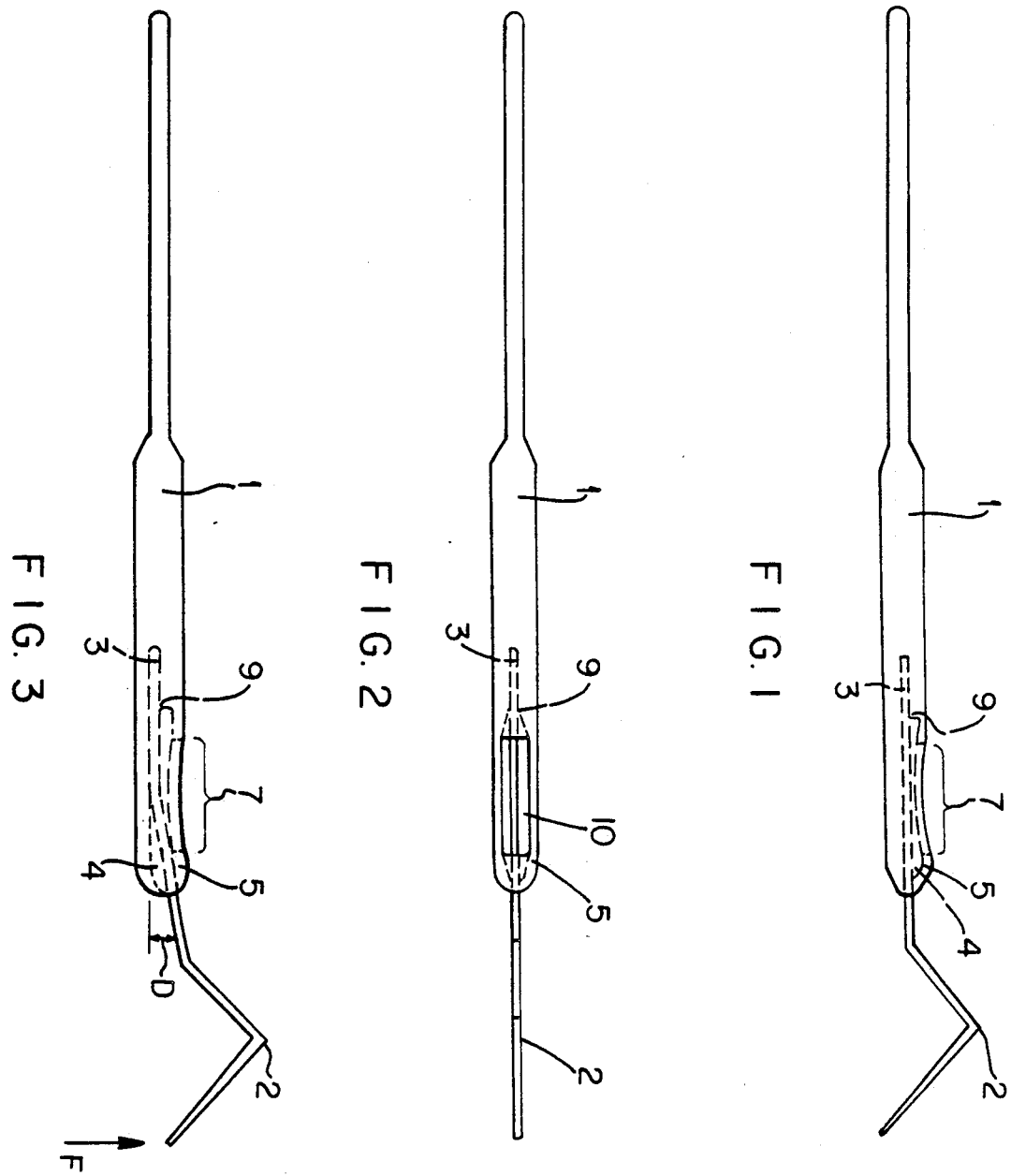

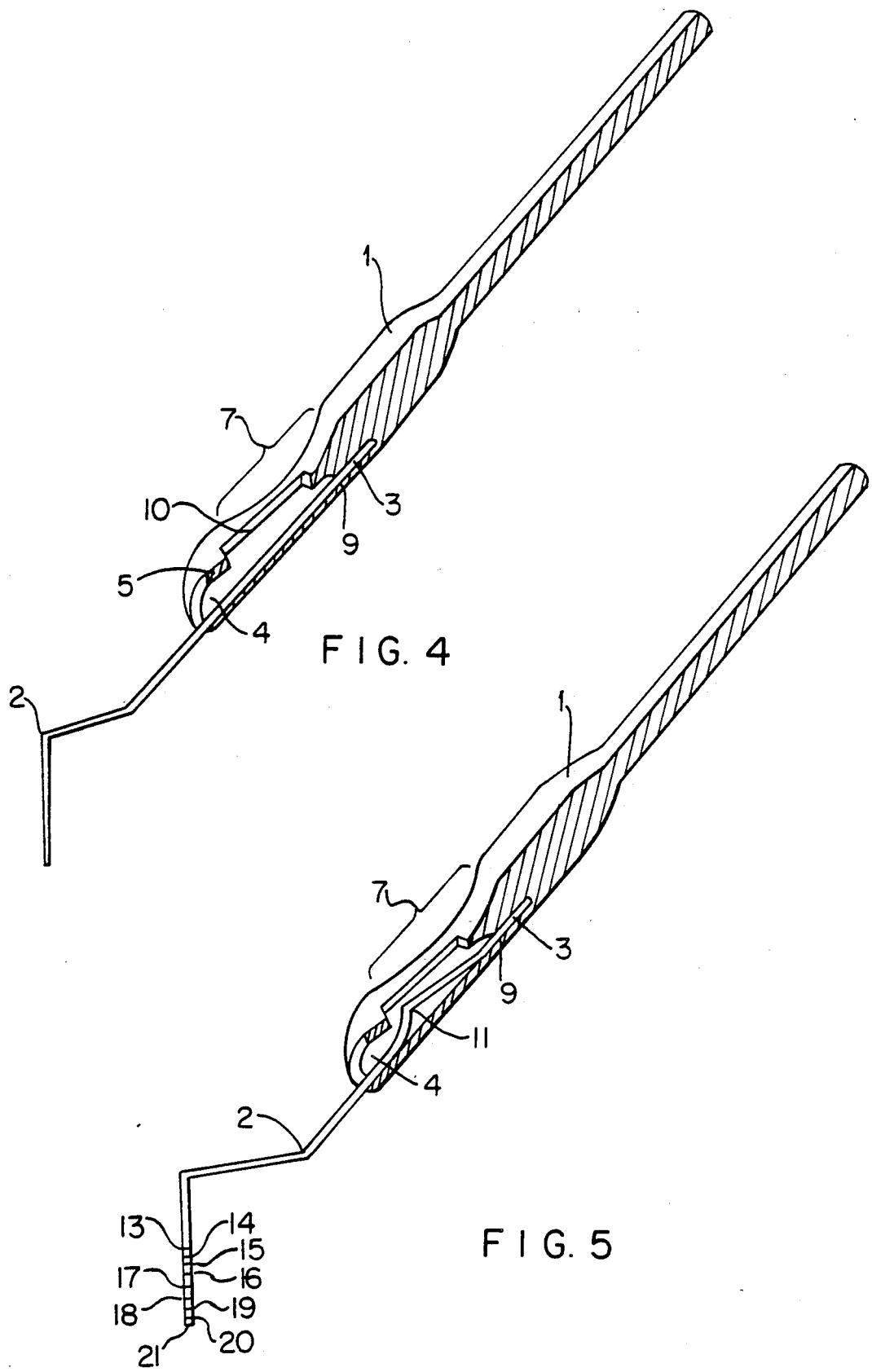

PERIODONTAL PROBE

BACKGROUND OF THE INVENTION

1. Field of the Invention

The present invention is directed toward simple handheld dental instruments that explore or probe the teeth and gums, and more particularly to such instruments that require the user to apply a minimum, maximum or consistent pressure to the instrument during use to obtain consistent professional results.

2. Prior Art Statement

Dental instruments have been in existence for as long as the art of dentistry has been practiced. Since the vast majority of these instruments are handheld, the effectiveness of their use is greatly dependent upon the skill and consistency of their user. As exemplified by dental probes, explorers and curettes the effectiveness of these instruments is entirely predetermined by the consistency of the user. Curettes are hard and sharp, if too much pressure is used with the instrument, the user may do harm to the gingiva or scratch the tooth surface. If too little pressure is used, the curette will fail to remove undesired materials. With the use of dental probes or explorers the problems are similar, in that, if varying pressures are used, the results of the instrument will be inconsistent and unusable. This is especially true when differing states of gingival health are being sampled.

In the past, all prior art dental instruments depended upon the knowledge and skill of the user to circumvent these problems. Subsequently, complex instruments were developed which were tied into digital readout instruments to give monitored readings. Such instruments are exemplified by U.S. Pat. Nos. 4,182,312 to Mushabac, 4,665,621 to Ackerman et al, and 4,708,647 to Pippen et al. These, however, are bulky, require wiring and servicing and are extremely expensive. The current invention is unique in that it removes the need of a highly skilled user to rely upon touch, by providing a means of self-regulation directly within the dental instrument. Consistency is obtained through the use of present invention spring biased dental instruments, which prior art neither teaches nor suggetsts.

SUMMARY OF THE INVENTION

The present invention is directed toward a handheld dental instrument which automatically regulates the pressure at which the working end of the instrument engages a person's gingival sulcus. The instrument includes an extending probe that is spring biased into a set position. The bias of the probe is predetermined, and is designed to yield to a preset minimum force. The deformation of the instrument's spring bias keeps the force of the instrument consistent against any object. This consistent pressure assures that the instrument will work in the same manner and give the same results, time after time. Additionally, the consistency of the instrument will result in more accurate results and increase in the dentist's confidence while using the instrument.

BRIEF DESCRIPTION OF THE DRAWINGS

The present invention will be more fully understood by referring to the following detailed specifications, the above specification and the claims set forth herein, when taken in conjunction with the drawings hereto, wherein;

FIG. 1 shows a side view of one preferred embodiment of the probe of the present invention;

FIG. 2 shows a top view of the preferred embodiment addressed in FIG. 1;

FIG. 3 shows a side view of the preferred embodiment depicted in FIGS. 1 and 2, with the spring bias engaged by a Deforming Force;

FIG. 4 shows a cross sectional oblique view of the preferred embodiment of the probe addressed in FIGS. 1 and 2;

FIG. 5 shows a cross sectional oblique view of an optional preferred embodiment of the probe of the present invention; and, FIG. 6 shows a side view of another optional preferred embodiment of the present invention.

DETAILED DESCRIPTION OF THE INVENTION AND DRAWINGS

Figure 6:
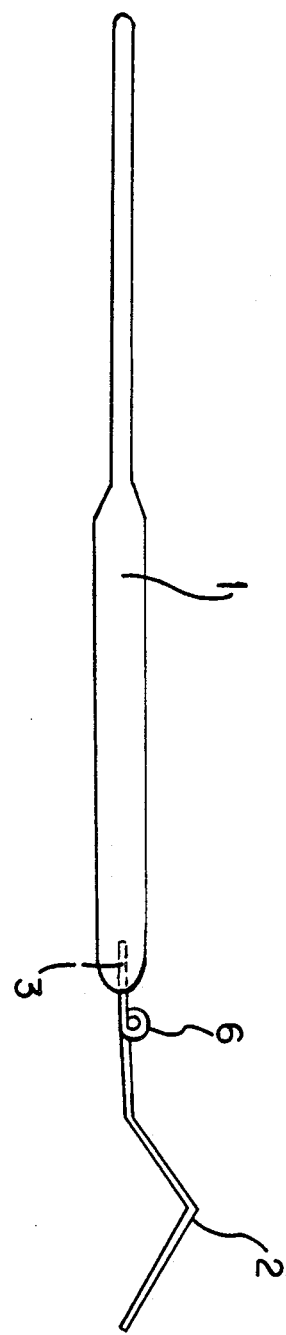

The present invention, as mentioned, is directed towards a dental instrument that automatically regulates the pressure at which the working end of the instrument engages a person's teeth, gums or gingival sulcus. In traditional handheld instruments such as curettes, explorers, probes, condensers, pluggers, scalers and the like, the pressures applied to the instruments greatly vary as the dentist maneuvers the instruments around the contours of a person's teeth. The varying pressures must consistently be regulated by the dentist's hand, to assure the effectiveness and reliability of the instrument. The working end of most dental instruments are designed to be hard and narrow, so that they can be positioned around a person's teeth. As a result, if a dentist applies too much pressure to such instruments, the instrument can easily scratch a person's tooth, or cut a person's gums. In the case of a periodontal probe, too much pressure can cause the probe to pierce the friable epithelial attachment and actually probe the osseous level within the gum rather than the base of the sulcus. When too little pressure is applied, a periodontal probe can lodge on tooth accretions or tight gingival fibers, thereby giving you a false reading.

Traditionally the skill of a dentist's hand is the only controlling device that regulated the pressures applied to the dental instruments. The arbitrary judgement of the dentist alone determines if the instrument was being used forcefully enough to be effective, yet not overly forceful as to be inaccurate or potentially cause harm. As a result, the arbitrary judgements of dentists in the use of their instruments have led to large discrepancies in the practice of dentistry. There are many recommended dental standards used by all dentists in their evaluation of their patients dental health needs. Many of the dental standards are referenced from information gathered by a dentist through the use of various probing instruments. Since the pressure applied to these instruments by the denstists are arbitrary, the results often are arbitrary. With arbitrary results, the dental standards referenced with these results are meaningless.

It is with these problems in mind, that the current invention removes the arbitrariness from the pressures applied to dental instruments. As a result, the instruments work in the same manner and give the same results, time after time. The improved consistency leads to better use, better referencing of dental standards and improved confidence and performance by dentists.

Referring now to FIG. 1 there is shown a side view of one preferred embodiment of the invention dental instrument. FIG. 1 shows the instrument at rest and shows the spring biased relational positioning of the substantially linear elongated member 1 and the narrow probe 2. FIG. 2 is the top view of the same preferred embodiment and shows the optional tactile area 10 within the finger rest area 7 of the elongated member 1. The tactile area 10 allows the holder of the instrument to feel the probe 2 when the probe 2 is deflected to its maximum position. The elastic deflection characteristics of the present invention are shown in FIG. 3. FIG. 3 is a side view of the preferred embodiment expressed in FIGS. 1 and 2 with a Force F being applied to the narrow probe 2. The Force F deforms the spring bias of the narrow probe 2. The narrow probe 2 deforms from its original position a Distance D. The amount of the deformation D is directly proportional to the Force F applied to the narrow probe 2. The maximum deformation Distance D is limited by the upper wall 5 of the non-attached enveloped area 4, which acts as a stop to the springed cantilever action. The resistance of the spring bias of the narrow probe 2, to the deforming Force F is consistant throughout the maximum deformation Distance D.

Referring now to FIG. 4, there is shown an oblique cross sectional view of the same embodiment of FIGS. 1 and 2 cut along its midsection. FIG. 4 best depicts the interactions of the substantially linear elongated member 1 and the narrow probe 2 that form the basis of this invention. As shown from FIG. 4, the narrow probe 2 is partially enveloped by the substantially linear elongated member 1. A length 3 of the substantially linear elongated member is permanently affixed to the narrow probe 2. However, an area 4 within the enveloping substantially linear elongated member 1 does not attach to the narrow probe 2 and allows for the limited free horizontal movement of the narrow probe 2 within the non-attached enveloped area 4. The non-attached enveloped area 4 diverges from the attached enveloped area 3 at point 9 and the amount of vertical free movement allowed the narrow probe 2 by the non-attached enveloped area 4 increases from the divergence point 9 to the end of the substantially linear elongated member 1. The divergence of the substantially linear elongated member 1 from the attached enveloped area 3 to an unattached enveloped area 4 creates a situation in where the narrow probe 2 acts as a spring bias cantilever, based on at the divergence point 9. The extent of the spring action caused by the cantilever positioning of the narrow probe 2 is limited by the upper wall 5 of the non-attached enveloped area 4. When the narrow probe 2 is engaging the upper wall 5, the holder of the instrument can feel that the narrow probe 2 is in its maximum extended position through physical contact with the narrow probe 2 via the tactile area 10 that extends through part of the finger rest area 7.

FIG. 5 is an oblique cross sectional view of a slightly differing embodiment than is shown in FIGS. 1, 2, 3 and 4. FIG. 5 shows the added feature of a convoluted probe 2 that has a high point 11 that corresponds to the area below that tactile area 10. The convoluted shape of the probe 2 adds to the spring means of the cantilever configuration and makes the probe 2 easier to feel by the holder when the probe's high point 11 engages the user's finger through the tactile area 10, as the probe 2 is elastically deformed. FIG. 5 also shows the narrow probe 2 to be shaped into a periodontal depth probe. In the configuration end of the narrow probe 2, is rounded and narrow probe 2 is periodically marked in units of length. The units of length standard to periodontal depth probes are represented by markings of one millimeteer 20, two millimeters 21, three millimeters 18, five millimeters 17, seven millimeters 16, eight millimeters 15, nine millimeters 14 and ten millimeters 13. The obvious close orientation of these markings on the peridontal depth probe further demonstrate how critical the pressure applied to a dental instrument is in obtaining an accurate measured result.

FIG. 6 shows a differing preferred embodiment of the present invention. FIG. 6 shows a narrow probe 2 that is spring biased by coiled configuration 6 rather than the cantilever of FIGS. 1, 2, 3, 4 and 5. The coiled configuration action of the narrow probe 2 is permanently affixed 3 to the substantially linear elongated member 1 and acquires its spring biased deformational action from a prior calibrated coiled configuration 6, directly manufactured into the narrow probe 2. The calibrated coiled configuration 6 elastically deforms and provides consistent pressure to the narrow probe 2 in response to a range of varying forces applied to the narrow probe 2. The embodiments of FIG. 1, 2, 3, 4, 5 and 6 show only a few examples of how the present invention can be incorporated into dental instruments. As compared to current dental instruments, the present invention can improve the instruments dentists currently use to clean and scrape teeth and gums, pack abnd test fillings, explore root canals, condense root canal fillings and search for cavities, as well as improve most periodontal probes that measure the depths within, and distances between, both gums and teeth (gingival sulcus or pocket).

It becomes obvious that the narrow probe of the present invention can derive its predetermined spring function from numerous independent and incorporated spring sources, and that there can be numerous configurations assigned to the shape, form and locations, of the spring action. Additionally, numerous configurations and materials can be used in the creation of the narrow probe or the substantially linear elongated member. It is therefore understood that within the scope of the appended claims, the invention may be practiced otherwise than is specifically described within.

What is claimed is:

1. A dental instrument which comprises:
   (a) a substantially linear elongated member having two ends, one said end having a relief formed therein creating a hollowed region; said elongated member having an orifice thereon that intersects said hollowed region; and,
   (b) a narrow probe having two ends, first said end of which depending from said elongated member within said hollowed region and the opposing second said end extending through and beyond said hollowed region, said narrow probe's first end attachment to said elongated member creating a cantilever, giving said narrow probe a spring constant valve that allows said narrow probe to elastically deform when engaged by a predetermined range of forces, the range of said elastic deformation being limited by the inside surfaces of said hollowed region.

2. The dental instrument of claim 1 wherein said orifice allows a user's finger to have a tactile sensation from said narrow probe, when said narrow probe is deformed to its maximum extent within said hollowed region.

3. The dental instrument of claim 1 wherein said narrow probe has a highpoint formed thereon, said highpoint being the first part of said narrow probe to cause a tactile sensation to a user's finger through said orifice.

4. The dental instrument of claim 1 wherein said orifice is formed within the area of a finger rest.

5. The dental instrument of claim 1 wherein said narrow probe causes a tactile sensation to a user when said narrow probe is deformed by a force of between approximately 25 grams to 50 grams.

6. The dental instrument of claim 1 wherein said second end of said narrow probe is periodically marked in units of length to create a periodontal depth probe.

7. The dental instrument of claim 1 wherein said second end of said narrow probe is sharpened creating an endodontic explorer or condenser.

8. The dental instrument of claim 1 wherein said second end of said narrow probe is blunt and shaped to create an amalgam packer.

* * * * *